United States Patent [19]

Rotman

[11] Patent Number: 5,472,846
[45] Date of Patent: Dec. 5, 1995

[54] TEST KIT AND METHOD FOR AMPLIFICATION AND DETECTION OF ANTIGEN CELLS

[76] Inventor: M. Boris Rotman, 1062 E. Shore Rd., Jamestown, R.I. 02835

[21] Appl. No.: 292,416

[22] Filed: Aug. 18, 1994

[51] Int. Cl.$^6$ .................................................. G01N 33/53
[52] U.S. Cl. ........................... 435/7.23; 435/7.2; 435/7.5; 435/7.9; 435/7.91; 435/29; 435/34; 435/839; 435/834; 435/848; 435/874; 435/881; 435/883; 435/5; 435/6; 436/527; 436/531; 436/813
[58] Field of Search ........................... 435/5, 6, 7.1, 7.2, 435/7.23, 7.5, 7.9, 7.91, 7.92, 29, 34, 839, 834, 848, 874, 881, 883, 966; 436/527, 531, 807, 808, 813

[56] References Cited

U.S. PATENT DOCUMENTS

| | | | |
|---|---|---|---|
| Re. 31,712 | 10/1984 | Giese | 428/467 |
| 4,002,532 | 1/1977 | Weltman et al. | 436/513 |
| 4,478,914 | 10/1984 | Giese | 428/407 |
| 4,656,252 | 4/1987 | Giese | 435/7.5 |

OTHER PUBLICATIONS

Premi, Thomas, MD and Battifora, Hector, MD. "Keratins Versus Epithelial Membrane Antigen in Tumor Diagnosis: An Immunohistochemical Comparison of Five Monoclonal Antibodies", *Human Pathology*, vol. 18, No. 7, Jul. 1987, pp. 728–734.

*Primary Examiner*—Carol A. Spiegel
*Attorney, Agent, or Firm*—David Knaack

[57] ABSTRACT

A test kit and method for the amplification and detection of specific antigen cells using a probe. The method includes reacting the probe-specific cells with enzyme-conjugated molecules to form separate molecules. The specific antigen cells are mixed with a selected antibiotic which antibiotic is adversely affected by the enzyme in the reporter molecules and incubating the mixture to promote a bacterial chain reaction forming satellite colonies of bacteria microcolonies about the specific cells which amplifies the cells. The method then includes detecting the amplified probe-specific cells by observing the satellite colonies.

9 Claims, No Drawings

TEST KIT AND METHOD FOR AMPLIFICATION AND DETECTION OF ANTIGEN CELLS

BACKGROUND OF THE INVENTION

Highly sensitive detection systems have become important analytical tools in medical diagnostics and biological research, as illustrated by the use of fluorescence immunochemistry, flow cytometry, enzyme-linked immunocytochemistry, and in situ DNA or RNA hybridization. In some areas, nevertheless, there is a substantial interest in developing new cost-effective techniques which extend presently available detection limits. For example, some patients with early-stage cancer have small number of metastatic tumor cells in their bone marrow which escape detection by routine procedures such as bone scan, biochemical analysis, and cytological examinations. The most frequently used methodology for detecting these rare tumor cells, usually referred as occult micrometastases, is immunocytochemistry (Premi, T., and Battifora, H. Human Pathol. 18, 728–734, 1987, hereby incorporated as a reference). At present, however, immunocytochemistry cannot be used on a routine basis because it is extremely labor-intensive. For example, a histopathology-trained technician necessitates about four hours of microscopic scanning to analyze a specimen (and appropriate controls) containing less than 10 malignant cells per million bone marrow cells.

Automated screening techniques, such as flow cytometry and computerized image analysis, not only require extensive capital investments but have been found to be less sensitive than conventional immunocytochemistry. It is clear, therefore, that in this particular field there is a need for simple and cost-effective techniques capable of detecting malignant cells present at low frequencies in clinical specimens of blood or bone marrow. Other clinical fields may also benefit from such techniques because, for example, they could provide sensitive means to: 1) detect early relapse in cancer patients; 2) test effectiveness of adjuvant treatments throughout therapy of patients with metastatic disease; 3) monitor the presence of tumor cells in blood or bone marrow used for autologous transplantation to prevent infusion of tumor cells into patients; 4) track circulating genetically engineered cells in patients.

Similarly, simple, more sensitive techniques could find clinical and investigational applications for lowering the detection levels of biologically important macromolecules which are presently analyzed using enzyme-linked or radioactive probes. For example, amplification-visualization techniques currently used for DNA-probe detection include enzyme-catalyzed reactions yielding chemiluminescent products, fluorescent products, or colored insoluble precipitates. Typically, in these techniques, a labeled nucleic acid probe is annealed to a complementary DNA or RNA target sequence which is either in solution or immobilized on an inert support. The binding of the labeled probe (usually an oligonucleotide which either contains a radioactive element or is attached to an enzyme via conventional ligand-binding protein technology) reports the presence or absence of a the target sequence in the reaction mixture. Examples of clinical applications using DNA probe amplification-visualization are tests for viruses, oncogenes, or multiple resistance genes using enzyme-labeled DNA probes.

SUMMARY OF THE INVENTION

The invention relates to a test kit and method for the amplification and detection by visualization of biomolecular probes, such as but not limited to, antibodies (monoclonal and polyclonal), binding proteins, lectins and oligonucleotides.

It is one object of this invention to provide a relatively simply and low cost methodology for extending the practical detection limits of currently used biomolecular probes.

The invention concerns a method for the amplification and detection of specific antigen cells using a biomolecular probe, which method comprises providing an analyte which includes therein probe-specific cells to be amplified and detected; reacting the probe-specific cells of the analyte with enzyme-conjugated probe molecules to form cell-enzyme-reporter molecules; exposing the cell-enzyme-reporter molecules to a selected antibiotic and with antibiotic-sensitive bacteria cells and with the selected antibiotic adapted to be destroyed by the enzyme of the reporter molecule; incubating the treated mixture of the cell-enzyme-reporter molecules and the antibiotic to promote a bacterial chain reaction forming a satellite colony of bacteria microcolonies about the probe-specific cells which amplifies the presence of the probe-specific cells; and detecting the amplified, probe-specific cells by observation of the satellite colony.

The invention includes a test kit useful to carry out this method, which test kit comprises an enzyme-conjugated probe molecule adapted to react with probe-specific cells of an analyte to form cell-enzyme-reporter molecules; a solid matrix-coated surface which coated surface comprises a selected antibiotic adapted to be destroyed by the enzyme of the reporter molecule and selected antibiotic-sensitive bacteria cells whereby the coated surface is exposed to the reporter molecule and incubated to form a satellite colony of bacteria microcolonies which are amplified and then detected.

The underlying basis of the invention is the bacterial chain reaction (BCR), an innovative amplification-visualization system. The BCR utilizes living bacteria to amplify signals from reporter molecules bound to an analyte. For example, enzymelabeled monoclonal antibodies directed against particular tumor antigens may serve as reporter molecules to detect and quantify specific tumor cells. Under appropriate conditions, a tumor cell coated with reporter molecules triggers nearby bacterial cells to initiate a proliferative chain reaction resulting in a visible cluster of bacterial microcolonies (termed here "satellite colony") surrounding the tumor cell. Thus, the amplification effected by the BCR has considerable practical importance because it is naturally coupled to visual signals (i.e., satellite colonies) reporting the presence of rare tumor cells in a large population of normal cells. In this particular example, it is possible to obtain quantitative estimates of the rare cells (i.e., antibody-binding cells present in the analyte) by simply enumerating satellite colonies.

In one embodiment of the invention, the analyte (typically a suspension of human or animal cells containing a very small percentage (e.g., 0.001%) of probe-specific cells) is treated so as to coat the specific cells with reporter molecules suitable for the BCR. For example, a cellular analyte is sequentially treated with specific monoclonal antibodies and a covalent conjugate of β-lactamase I and antimouse IgG or lgM immunoglobulin. These conjugates can be obtained by a variety of methodologies, and the immunoglobulin is usually produced in animal species other than mouse, e.g., rabbit, goat, guinea pig or horse. Between each of the treatments, the analyte is washed several times with phosphate-buffered saline (PBS) containing 1% bovine serum albumin (BSA). As a result of these treatments, probe-specific cells (in contrast to all other cells in the analyte) acquire a coat of β-lactamase I. At this stage, a sample of the analyte is added to melted soft agar (kept at 45° C.) containing penicillin V (a substrate hydrolyzed by β-lactamase I, and also an inducer of β-lactamase I synthesis in some bacterial species), and cells of a penicillin-sensitive bacterium carrying an inducible β-lactamase I operon or a penicillin-sensitive bacteria genetically engineered to carry an inducible β-lactamase I operon. Under the conditions indicated above, probe-specific cells are detectable because their newly acquired enzyme coating hydrolyzes antibiotic in the immediate vicinity of the probe-specific cell triggering a proliferative chain reaction among nearby bacteria.

The BCR is the result of several interconnected events, some predictable others unexpected. For the given example, these events are: i) the penicillin concentration near a β-lactamase I-coated cell is drastically lowered because of enzymatic degradation; ii) as the local penicillin concentration falls below certain threshold, bacteria in the vicinity of individual β-lactamase I-coated cells start proliferating; iii) proliferating cells, in contrast to stationary bacterial cells, are induced by penicillin to produce β-lactamases; iv) bacteria synthesizing β-lactamases become less sensitive to penicillin; v) local penicillin concentration is further lowered by the bacterial enzymes; vi) further cycles of bacterial proliferation and induction occur. The overall result (after several hours of incubation) is formation of a satellite colony surrounding the probe-specific cells present in the analyte. A satellite colony typically consists of 5–100 bacterial microcolonies of different sizes (range 0.1–2.0 mm) arranged in a circular pattern with large microcolonies located near the center of the satellite colony, and proportionally smaller microcolonies towards the periphery. This characteristic morphology of a satellite colony (which is independent of overall colony dimension and number of microcolonies within the satellite colony) results from a concentration gradient of antibiotic causing rapid proliferation of bacteria near an enzyme-coated cell, as compared to bacteria further away from the cell. The morphology plays an important role in the BCR assay because bacterial contaminations do not interfere with the assay since they grow as single colonies, i.e., they do not produce satellite colonies.

In another embodiment of the invention, probe-specific cells to be analyzed are present in cell populations (or tissue sections) fixed on a surface such as a microscope slide. This type of analyte presentation is often encountered when clinical specimens, such as bone marrow or circulating leukocytes, are used for histopathological or immunocytochemical examinations. As in the previous embodiment, the cells are treated so as to coat them with an enzyme suitable for the BCR. In this case, however, the treatment is applied by sequentially dipping the slides in reagent solutions. After treatment, the slides are covered with a thin layer of melted soft agar containing antibiotic and bacteria. After a few hours of incubation, satellite colonies appear at discrete locations around probe-specific cells. After marking the location of the satellite colonies on the slide and removing the soft agar layer, the results of the BCR assay can be directly verified by conventional cytochemical techniques. For example, the slide may be counterstained with a fluorescence-labeled monoclonal antibody to ascertain the specificity of the cells reported by satellite colonies. Alternatively, the reported cells can be scraped off, and analyzed for specific DNA or RNA sequences using the polymerase chain reaction.

In a different embodiment of the invention. the analyte is immobilized on a matrix such as a membrane filter. This type of analyte presentation is often encountered during analytical separation of proteins, nucleic acids and other macromolecules by electrophoresis. As in previous embodiments, the matrix is treated with reagents designed to specifically coat the analyte with a suitable enzyme. Subsequently, the matrix is covered with a thin layer of melted soft agar containing antibiotic and bacteria. After a few hours of incubation, satellite bacterial colonies mark the analyte location on the matrix.

Although this invention has been reduced to practice using β-lactamase I and penicillin V as the enzyme-antibiotic combination, several other combinations can be used. The prerequisites for using an enzyme-antibiotic combination for the BCR are: (1) the antibiotic has to be either cytotoxic or cytostatic for the particular species of bacteria used in the system, and (2) the enzyme has to obliterate specifically the antibiotic activity. Examples of enzyme-antibiotic combinations suitable for the BCR (but not limited to these examples) are shown in Table 1.

TABLE 1

Examples of enzyme-antibiotic combinations suitable for the BCR

| Antibiotic(s) | Enzymes |
| --- | --- |
| Cephalosporins | β-lactamases II |
| Chloramphenicol, kanamycin | acetyltransferases, adenylyltransferases |
| Formycin | adenosine deaminase |
| Penicillins | β-lactamases I, penicillinases |
| Puromycin | nucleosidases |
| Streptomycin, gentamycin | phosphotransferases |

It should be mentioned that for certain enzyme-antibiotic combinations it is possible to separate the antibiotic-destroying activity from the inducer activity. For example, a hybrid molecule consisting of cephalosporin (an antibiotic hydrolyzed by β-lactamase II) and isopropyl-β-D-galactoside (an inducer of the lac promoter) will liberate isopropyl-β-D-galactoside in the immediate surroundings of an analyte coated with β-lactamase II. Under these conditions, a bacterium carrying a lac promoter upstream of the β-lactamase II gene will begin to synthesize β-lactamase II in response to the inducer liberated near the analyte. This action, in turn, will increase local hydrolysis of cephalosporin-isopropyl-β-D-galactoside thus intensifying the BCR.

With regard to bacteria, numerous species can be used for the BCR. The following represent examples of suitable species (but not limited to these): *Bacillus subtilis, Bacillus cereus, Escherichia cloacae, Providencia stuartii, Pseudomonas aeruginosa, Serratia marcescens, Sarcina lutea, Staphylococcus aureus.*

DETAILED DESCRIPTION OF THE PREFERRED EMBODIMENTS

The present invention comprises high sensitivity assays for a variety of analytes employing the BCR system to amplify and detect probes bound to analytes. In all instances, the end point is formation of satellite colonies reporting the presence, location, and number of specific analyte-binding probes. As defined herein, a probe comprises molecules capable of specifically binding a domain in the analyte. Examples of analyte-binding probes comprising proteinaceous substances (such as glycoproteins, lipoproteins and others) include specific antibody molecules (polyclonal, monoclonal, and fragments thereof), specific binding proteins (such as biotin-binding protein (avidin, streptavidin), carbohydrate-binding protein (lectins), and DNA-binding proteins), cell receptors, and transport proteins but not limited to these examples. Examples of analyte-binding probes comprising nucleic acids include natural or synthesized oligonucleotides complementary to sequences present in tissues of human, animal or plant origin, viruses, bacteria, plasmids, and in genetically-engineered organisms or manmade constructs.

The components and reagents of the BCR assay system of the present invention may be supplied (in aqueous or lyophilized form) in the form of a kit in which the simplicity and sensitivity of the assay are preserved. All necessary reagents can be added in excess to accelerate the reactions.

5.1 Analytes

The improved methods and novel design of the present invention can be used to determine the presence and quantity of a variety of analytes. Illustrative examples of such analytes include, but are not limited to, the following: 1) rare cells (of any species) with specific surface antigens (including hormones and other molecules recognized by cell receptors); 2) rare cells (of any species) producing or overproducing cytoplasmically certain proteins; 3) rare cells (of any species) containing abnormal DNA or RNA sequences; 4) rare cells containing abnormal amounts of certain messenger RNA; 5) macromolecules such as proteins or nucleic acid present in extremely small quantities as blots in solid supports (e.g., filter paper, nitrocellulose membranes, and polyacrylamide gels) commonly used to separate such macromolecules by chromatography or electrophoresis.

5.2 Enzyme-probe conjugates

Enzyme-probe conjugates can be prepared by a large variety of methods preserving the specificity and sensitivity of the particular probe as well as the catalytic activity of the enzyme. Preferred embodiments of this invention utilize enzymelabeled probes prepared by covalent conjugation with glutaraldehyde as described in U.S. Pat. No. 4,002,532, Jan. 11, 1977, hereby incorporated as a reference. Alternatively, enzymes can be directly conjugated to probes using one of the many methods described in the literature.

Indirect procedures for obtaining stable enzyme-probe complexes can also be used. These procedures are based on ligand-binding protein technology such as that developed for biotin-avidin or digoxigenin-antidigoxigenin technology. For example, an enzyme-streptavidin conjugate provides an intermediate to label proteinaceous probes containing biotin since streptavidin binds biotin with a high association constant. Biotin-containing probes can be easily synthesized by well known methods or in many instances are commercially available. Examples of biotin-labeled and digoxigenin-labeled probes include antibodies (polyclonal, monoclonal, or fragments thereof), oligonucleotides, lectins and binding proteins. This method is specially useful for enzyme-labeling oligonucleotide probes synthesized with biotin-labeled or digoxigenin-labeled nucleic acid precursors.

5.3 Bacteria

Either vegetative cells or spores may be used for the BCR assay. For example, *Sarcina lutea* cells are grown in Difco Heart Infusion broth at 37° C. Cultures are aerated in a tube roller, and harvested before reaching stationary phase. It should be noted that cryopreserved cultures are routinely used for the BCR assay. For cryopreservation, the cultures are mixed with glycerol (20% final concentration), divided in aliquots, and placed at −20° C. When using spores, cultures are allowed to reach stationary phase under conditions leading to sporulation. Spores are collected by centrifugation, washed in distilled water, and heated at 65° C. for 30 minutes. After heat treatment, spores are washed three times with distilled water and the heating step is repeated. Spore suspensions can be maintained at 0°–4° C. for several weeks.

6. EXAMPLE

ENUMERATION OF RARE TUMOR CELLS IN HUMAN BONE MARROW OR BLOOD SPECIMENS

This example illustrates a BCR assay for tumor cells present at extremely low frequency among normal bone marrow cells or peripheral blood leukocytes. To coat probe-specific cells with β-lactamase I, cells were treated sequentially with anticytokeratin monoclonal antibody specific for cytokeratin 18 (Sigma Chemical Co.) and a covalent conjugate of goat antimouse immunoglobulin (Sigma) and β-lactamase I (Sigma).

6.1 Preparation of analytes

Two-ml samples of blood or bone marrow specimens (collected with heparinized syringes) are diluted 1:2 with phosphate-buffered saline (PBS), and the nucleated cells are separated using Ficoll-Hypaque (Litton Bionetics, Inc.) density gradient centrifugation. After centrifugation, nucleated cells at the interface are collected, washed twice with PBS, resuspended in 0.5 ml PBS, and counted in a hemocytometer. Cellular viability is measured using fluorochromasia. Buffy coats from either blood or marrow specimens may be substituted for nucleated cells separated by density centrifugation. To this end, blood or bone marrow specimens are decanted for 10 min at room temperature, and the top layer containing mostly nucleated cells is separated. As before, cells are washed twice with PBS and counted. Typically, cell suspensions from buffy coats contain less than 10% red cells, an amount that does not interfere with the BCR assay. These observations are important because the invention can circumvent Ficoll-Hypaque separation, a costly, and time consuming step required for histology, immunocytochemistry and other methodologies.

Nucleated cells resuspended in PBS are fixed by adding an equal volume of ethanol under strong agitation (Vortex mixer), and letting the suspension incubate at room temperature for 30 minutes. The fixed cells are collected by centrifugation. Different monoclonal antibodies may require different fixation treatments. The fixed cells resuspended in PBS may be stored at 0°–4° C. for several days. Fixed cells can be kept in ethanol at −20° C. for several weeks.

6.2 Enzyme-probe covalent conjugates

Covalent conjugates were prepared following the procedure described in U.S. Pat. No. 4,002,532, Jan. 11, 1977, hereby incorporated as a reference. Fifty micrograms of goat antimouse IgG (whole molecule, adsorbed with human serum proteins, Sigma Chemical Co.) were conjugated with 410 micrograms of β-lactamase I (Sigma) in the presence of 0.02M glutaraldehyde. After 4 hours of incubation at room temperature, the reaction mixture was dialyzed extensively against PBS containing 0.05% sodium azide. The conjugate was separated from the reaction mixture using SEPHADEX™ G-200 chromatography.

6.3 BCR Assay

Suspensions of fixed cells were treated sequentially with specific monoclonal antibodies and enzyme-probe covalent conjugate. Between each treatment, the cells were washed twice with PBS-BSA. Typically, cells were treated with a dilution 1:100 of the anticytokeratin 18 monoclonal antibody for 30 min at room temperature, separated by centrifugation, and washed with PBS-BSA twice in the same manner. The cellular pellet was resuspended in a dilution (e.g., 1:500) of the enzyme-probe covalent conjugate, and incubated for 30 min at room temperature. After incubation, the cells were washed four times with PBS-BSA, and then added to 10 ml of melted soft agar (0.45% Difco heart infusion agar kept at 45° C.) containing penicillin V ($10^5$ units/ml) and $S.$ $lutea$ cells ($10^6$ cells/ml). After overnight incubation at 37° C., bacterial satellite colonies on the plate were counted using a dissecting microscope or a magnifying lens.

To test the specificity of the BCR assay, normal human nucleated cells from either blood or bone marrow were mixed with limiting numbers of cells from MCF-7, an established cell line originally isolated from a patient with metastatic mammary adenocarcinoma. Results showed that satellite colonies were present only on plates containing nucleated cells mixed with MCF-7 cells. In addition, controls missing either the monoclonal antibody or the antibody-enzyme complex did not have satellite colonies.

7. EXAMPLE

ENUMERATION OF RARE TUMOR CELLS IN HUMAN BONE MARROW OR BLOOD SPECIMENS FIXED ON MICROSCOPE SLIDES

This example illustrates the use of the invention for enumerating tumor cells present at extremely low frequency among normal bone marrow cells or peripheral blood leukocytes fixed on microscope slides. The reagents were identical to those used in the previous examples.

7.1 Preparation of analytes

Nucleated cells (prepared as indicated in Example 6 using either density centrifugation or bully coats) were deposited on polylysine-coated microscope slides (Sigma), allowed to dry at room temperature, and fixed by treatment with absolute ethanol for 30 minutes. Slides were stored for several weeks at −20° C.

7.2 BCR Assay

Slides containing the analyte were treated with horse serum for 30 minutes at room temperature to block nonspecific binding sites, and then treated sequentially with specific monoclonal antibodies, and enzyme-probe covalent conjugate by immersing the slides in the appropriate solutions. Between each treatment, the slides were washed by immersing them for 10 minutes in PBS-BSA. Typically, the slides were incubated for 30 min at room temperature in a 1:100 dilution of an anticytokeratin 18 IgGl monoclonal antibody (Sigma), washed twice, incubated for 30 min at room temperature in a dilution 1:500 of the enzyme-probe covalent conjugate, and then washed four times. After the treatment, the slides were placed on a Petri plate and covered with 14 ml of melted soft agar (0.45% Difco heart infusion agar kept at 45° C.) containing penicillin V ($10^5$ units per ml) and $S.$ $lutea$ cells ($10^6$ cells/ml). After overnight incubation at 37° C., bacterial satellite colonies marked the location of tumor cells coated with β-lactamase.

As before, the assay specificity was tested using MCF-7 cancer cells mixed with normal human nucleated cells from either blood or bone marrow. To identify MCF-7 cells, a fluorescein-labeled anticytokeratin 18 IgGl monoclonal antibody (Sigma) was used as the primary antibody. Results showed that satellite colonies were only present around MCF-7 cells which were easily recognized by their binding fluorescent monoclonal antibody.

8. EXAMPLE

DETECTION OF ANALYTES BLOTTED ON NITROCELLULOSE MEMBRANES

This example illustrates the use of the invention for detecting extremely small amounts of an analyte present as a blot on a nitrocellulose filter. Reagents were identical to those used in the previous examples.

Serial 1:2 dilutions of a fluorescence-labeled monoclonal antibody (Sigma) were spotted on a strip of nitrocellulose filter (BA-85; Bio-Rad Ltd.) using a 2-microliter volume for each dilution. The filter was allowed to dry at room temperature for 30 minutes, and then immersed for one hour in 50 ml of a blocking solution (5% skim dry milk in PBS). The strip was removed from the blocking solution, and was covered with a dilution 1:500 of the enzyme-probe covalent. The strip was allowed to incubate at room temperature for 30 minutes in a covered tray and then washed extensively with PBS-BSA. To visualize the spots, the strip was covered with 14 ml of melted soft agar (0.45% Difco heart infusion agar kept at 45° C.) containing penicillin V ($10^5$ units per ml) and $S.$ $lutea$ cells ($10^6$ cells/ml). After overnight incubation at 37° C., bacterial satellite colonies were observed over most of the spots. The sensitivity of the invention was clearly demonstrated by the fact that spots containing antibody concentrations well below that detectable by fluorescence were nevertheless visualized by the presence of satellite colonies Control spots lacking the analyte did not show satellite colonies.

9. EXAMPLE

ENUMERATION OF RARE TUMOR CELLS IN HUMAN BONE MARROW OR BLOOD SPECIMENS

This example illustrates the use of secondary antibody-enzyme complex prepared by the avidin-biotin methodology. As in Example 6, the assay was used to enumerate tumor cells present at extremely low frequency among normal bone marrow cells or peripheral blood leukocytes. The probe was an anticykeratin monoclonal IgM antibody (clone 35βH11) specific for low molecular weight cytokeratin 8 (Dako Corp.).

9.1 Preparation of analytes

Nucleated cells were prepared as indicated above (Example 6) using either density centrifugation or buffy coats.

9.2. Secondary antibody-enzyme complex

Covalent conjugates were prepared following the procedure described in U.S. Pat. No. 4,002,532, Jan. 11, 1977, hereby incorporated as a reference. Fifty micrograms of streptavidin (Sigma Chemical Co.) were conjugated to 200 micrograms of β-lactamase I (Sigma Chemical Co.) in the presence of 0.005M glutaraldehyde. After 4.5 hours of incubation at room temperature, the reaction mixture was dialyzed extensively against PBS containing 0.1% sodium azide. Bovine serum albumin was added to the conjugate to make a final concentration of 1 mg/ml.

9.3 BCR Assay

Suspensions of fixed cells were treated sequentially with anticykeratin 8 monoclonal IgM antibody, biotinylated rabbit, anti-mouse IgM immunoglobulin (whole molecule, adsorbed with human serum proteins, Sigma Chemical Co.), and streptavidin-enzyme conjugate. Between each treatment, the cells were washed twice with PBS-BSA. Typically, cells were treated with a dilution 1:50 of the anticytokeratin 8 monoclonal antibody for 30 min at room temperature, separated by centrifugation, and washed with PBS-BSA twice in the same manner. The cellular pellet was resuspended in a dilution (e.g., 1:100) of the rabbit anti-mouse IgM immunoglobulin, and the washing procedure repeated. Finally, the cells were incubated with the streptavidin-enzyme conjugate for 30 min at room temperature. After incubation, the cells were washed four times with PBS-BSA, and then added to 10 ml of melted soft agar (0.45% Difco heart infusion agar kept at 45° C.) containing penicillin V ($10^5$ units/ml) and *S. lutea* cells ($10^6$ cells/ml). After overnight incubation at 37° C., bacterial satellite colonies on the plate were counted using a dissecting microscope or a magnifying lens.

The specificity of the BCR assay was tested as indicated above (Example 6) using MCF-7 tumor cells.

What is claimed is:

1. A method for determining a preselected subpopulation of cells comprising a characteristic cell surface antigen in a population of cells which method comprises (a) providing a sample comprising said population of cells;

(b) contacting the sample with a probe comprising an enzyme conjugated to a specific binder which specifically binds to the characteristic cell surface antigen to form enzyme-coated cells, wherein the enzyme is capable of destroying a preselected antibiotic;

(c) contacting the sample of step (b) with a homogenous agar layer comprising (i) the preselected antibiotic and (ii) a sample of bacteria whose growth is inhibited by the preselected antibiotic to form a culture medium;

(d) incubating the culture medium at a temperature and for a time sufficient to provide for satellite growth of the bacteria, whereto the satellite growth consists of 5–100 bacterial colonies ranging in size from 0.1–2.0 mm clustered around the enzyme-coated cells in a circular pattern; and (e) determining the preselected subpopulation of cells comprising the characteristic cell surface antigen by correlating the occurrence of the satellite growth to the presence or amount of the preselected subpopulation of cells comprising the characteristic cell surface antigen in the sample.

2. The method of claim 1 wherein the sample of said population of cells comprises a suspension of mammalian cells and the characteristic cell surface antigen of the preselected subpopulation of cells is a known tumor marker.

3. The method of claim 1 wherein the enzyme is selected from the group consisting of β-lactamase, β-galactosidase, glucosidase, esterase, acetyltransferase, adenyltransferase, adenosine deaminase, penicillinase, nucleosidase, and phosphotransferase.

4. The method of claim 1 wherein the preselected antibiotic is selected from the group consisting of cephalosporins, chloramphenicol, kanamycin, formycin, penicillins, puromycin, streptomycin, and gentamycin.

5. The method of claim 1 wherein said sample is blood or bone marrow.

6. The method of claim 1 wherein the enzyme is β-lactamase.

7. The method of claim 1 wherein the bacteria are selected from the group consisting of *Bacillus subtilis, Bacillus cereus, Escherichia cloacae, Providencia stuartii, Pseudomonas aeruginosa, Serratia marcescens, Sarcina lutea*, and *Staphylococcus aureus*.

8. The method of claim 1 wherein the specific binder is a murine IgG monoclonal antibody and the enzyme is indirectly conjugated thereto through antimouse IgG antibody.

9. The method of claim 1 wherein the characteristic cell surface antigen is cytokeratin and the specific binder is anticytokeratin monoclonal antibody.

* * * * *